United States Patent [19]

Altshuler

[11] 4,363,319
[45] Dec. 14, 1982

[54] READY-TO-USE BANDAGE INCORPORATING A COAGULANT COMPOSITION AND METHOD OF PREPARING SAME

[75] Inventor: John H. Altshuler, Englewood, Colo.

[73] Assignee: Applied Medical Devices, Inc., Englewood, Colo.

[21] Appl. No.: 255,953

[22] Filed: Apr. 20, 1981

Related U.S. Application Data

[63] Continuation-in-part of Ser. No. 164,821, Jun. 30, 1980, abandoned.

[51] Int. Cl.³ ............................................. A61L 15/00
[52] U.S. Cl. .................................. 128/156; 206/570; 424/28; 435/214
[58] Field of Search ............................... 128/155–156, 128/171, 260, 261; 206/570, 440, 441; 435/188, 214; 424/94, 101, 28

[56] References Cited

U.S. PATENT DOCUMENTS

| | | | |
|---|---|---|---|
| 2,433,299 | 12/1947 | Seegers | 435/188 |
| 2,442,111 | 5/1948 | Beardsley | 128/156 |
| 3,317,376 | 5/1967 | Schattner | . |
| 3,328,259 | 6/1967 | Anderson | . |
| 3,342,183 | 9/1967 | Edenbaum | 128/156 |
| 3,731,683 | 5/1973 | Zaffaroni | 128/156 |
| 3,937,223 | 2/1976 | Roth | 128/156 |
| 4,022,203 | 5/1977 | Ackley | 128/156 |

Primary Examiner—C. Fred Rosenbaum
Attorney, Agent, or Firm—Fidelman, Wolffe & Waldron

[57] ABSTRACT

A prepackaged coagulant composition and method of preparing same has been devised for use in direct or topical application to wounds so as to cause superficial clotting in which thrombin is combined with special preservatives and a saline solution. A ready-to-use bandage is saturated with the resultant solution, sealed and stored so as not to lose its reactive properties with the fibrinogen in the blood when applied to a wound or cut.

16 Claims, 3 Drawing Figures

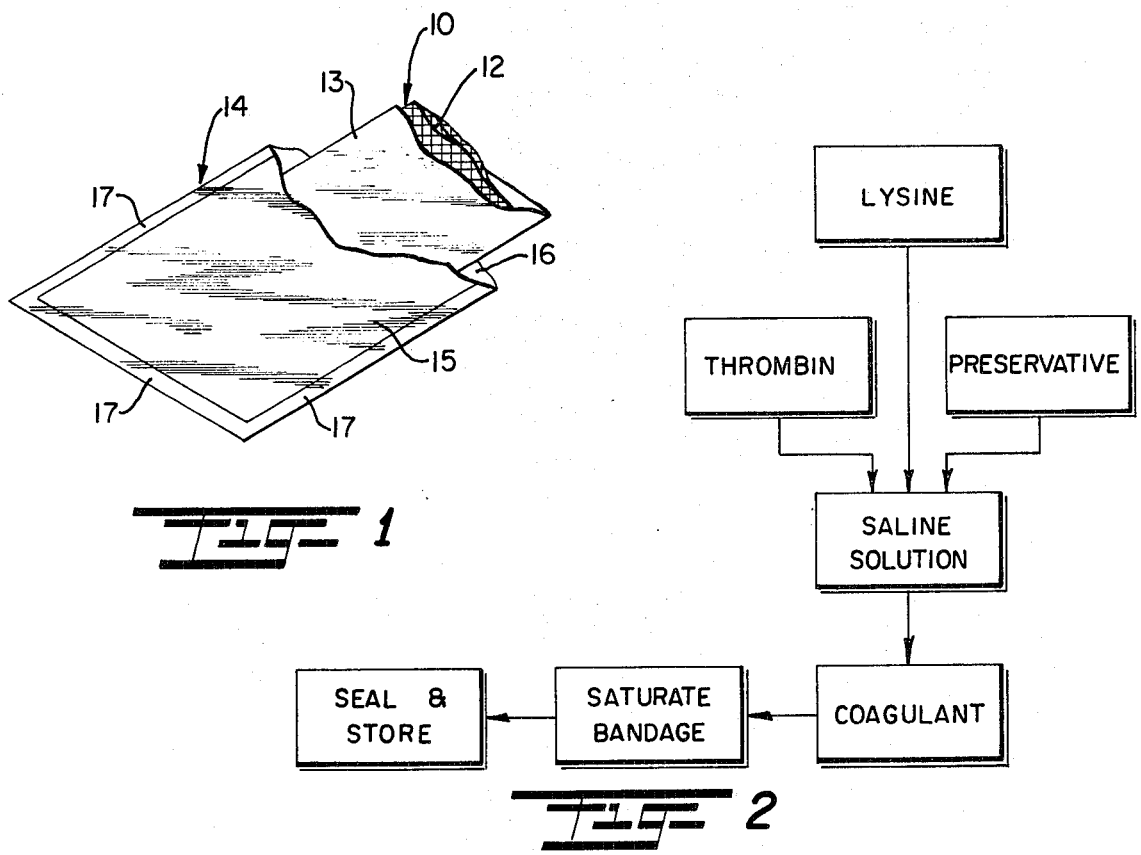
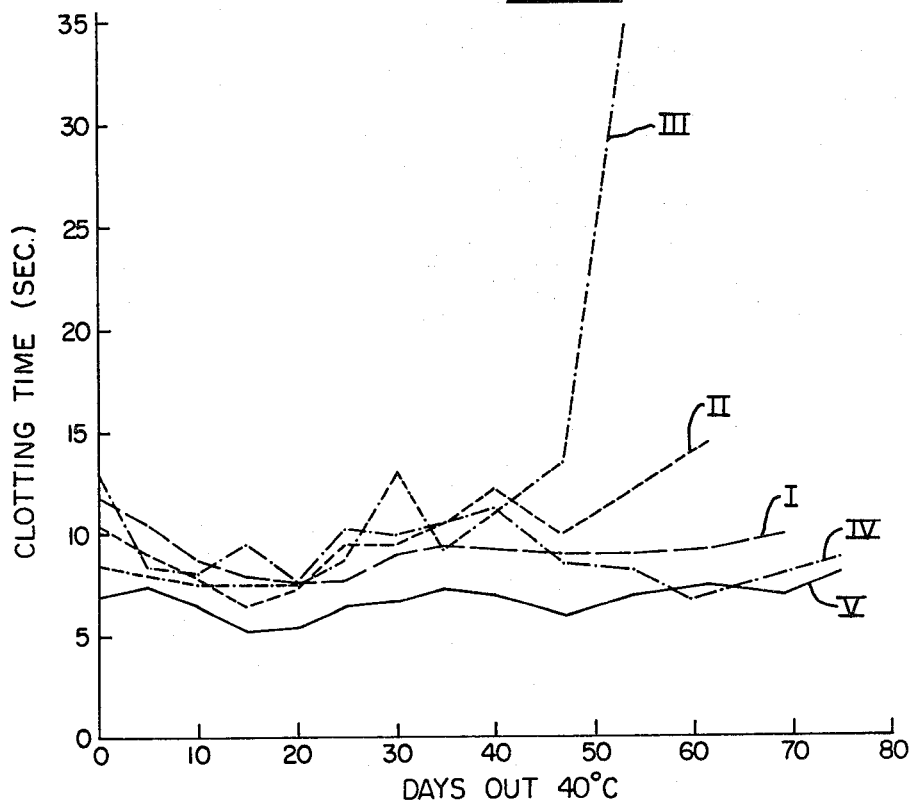

READY-TO-USE BANDAGE INCORPORATING A COAGULANT COMPOSITION AND METHOD OF PREPARING SAME

This application is a continuation-in-part of Ser. No. 164,821 filed June 30, 1980, now abandoned.

This invention relates to coagulants or clotting agents and more particularly relates to prepackaged bandages or absorbent pads saturated with a coagulant solution so as to be effective in clotting blood at the site of a wound in a reliable and efficient manner.

BACKGROUND AND FIELD OF THE INVENTION

Treated bandages or patches have been devised in the past as aids in stopping the flow of blood from wounds, cuts, scratches and the like. Generally, the approach taken has been to formulate a composition which includes a clotting agent with or without a germicidal or antiseptic agent and to saturate the pad or gauze strip on the bandage with that solution. For instance, U.S. Pat. No. to Curtis 2,579,367 discloses the formulation of a bandage in which a proteinaceous aqueous solution or paste is applied to the area to be treated, followed by the application of a protein coagulant which will be converted into an insoluble semipermeable artificial eschar. The suggested composition of the protein coagulant in that patent is from selected metal salts including water soluble salts of divalent zinc, manganese and cobalt and specifically zinc acetate, cobalt sulfur and manganese sulfate. It is proposed that this composition be applied to a surgical gauze and permitted to dry after which the gauze is applied to a coating of the protein paste over a wound so that the paste reacts with the metal salt of the bandage to form a metal caseinate. Others have proposed the use of various types of bandages or pads treated with a clotting agent, such as, for example, U.S. Pat. Nos. to Beardsley 2,442,111; Zaffaroni 3,731,683; Edinbaum 3,342,183; Schattner 3,317,376; and Anderson 3,328,259. In the past, however, none have devised an effective method of preparing a prepackaged coagulation composition which by proper storage can be applied as a dressing to a wound and operate effectively to convert fibrinogen in the blood to a fibrin clot.

The importance of acting directly upon the fibrinogen can be best appreciated by a consideration of the blood coagulation mechanism. Generally speaking, the unaltered clotting factor, known as a proenzyme, is converted to an active enzyme which is capable in turn of converting thousands of substrate molecules into active enzymes. This initiates a chain reaction whereby activation of a single proenzyme molecule may lead to activation of the entire clotting mechanism. On the other hand, the fibrinolytic system in the body is antagonistic to the clotting mechanism and maintains a balance between clot formation and clot lysis. In the fibrinolytic system, a series of proenzymes when activated are converted to enzymes which are capable of dissolving blood clots, the dissolving or lytic enzyme being referred to as plasmin. However, many factors can occur to upset the balance between clot formation and clot lysis. It is not the purpose in discussing the background of this invention to consider those factors which may interrupt the chain reaction or sequence in clotting. It is important to recognize, however, that most desirably the clotting activity should occur at a low point in the sequence or chain reaction and specifically be at the site of the wound so that the coagulation mechanism will not be interrupted by other upsetting factors in the sequence. This approach will minimize the risk of the coagulating agent entering the bloodstream and cause the clotting to occur most rapidly and superficially at the site of the wound.

Thrombin is a sterile protein substance prepared from prothrombin through interaction with added thromboplastin usually in the presence of calcium. In concentrated form, it has a potent clotting effect on the blood and specifically in coagulating plasma fibrinogen converting same to a fibrin clot. Customarily, thrombin is available in powder form mixed with minor proportions of other ingredients, such as, sodium chloride, calcium chloride, glycine and benzethonium chloride to aid somewhat as a preservative when the thrombin is stored in dry or powdered form. It has been applied in the past in solution form directly to cuts or injuries or used in combination with other hemostatic agents, such as an absorbable gelatin sponge which is applied following the closure of a surgical incision and the sponge gradually absorbed over a long period. None, however, has satisfactorily devised a method or formulation of thrombin by which it can be prepackaged, sealed and stored in solution form for subsequent application to a wound. U.S. Pat. No. 2,433,299 to Siegers is directed to the preservation of thrombin by storage in a sucrose solution which together with a saline solution can be sprayed or applied to a bleeding tissue. If anything, however, this patent highlights the problems associated with the preservation of thrombin and the sucrose solution does not make it practically usable as a prepackaged substance for clotting.

A significant difficulty that must be appreciated is the need to provide a product capable of movement in commerce. The product must have an acceptable shelf life under thermal conditions to which a prepackaged plasma clotting composition may expect to be subjected.

SUMMARY OF THE INVENTION

It is, therefore, an object of the present invention to provide for a novel and improved coagulant composition and method of preparing same in prepackaged form for application to a cut or wound either internally or externally of the body.

It is another object of the present invention to provide for a novel and improved bandage containing a coagulant solution which, when applied to a wound, is capable of coagulating the blood while protecting against the entry of foreign particles and which can be easily removed from the skin without reopening the wound.

A further object of the present invention is to provide for a prepackaged thrombin solution which is conformable for use in combination with absorbent pads, dressings, bandages and the like and is capable of being preserved and stored over extended periods of time for future use in treating wounds or cuts in a safe, dependable manner.

A prepackaged coagulant composition and method of preparing same have been devised for use in both rapidly and effectively clotting blood. Dressings, bandages, absorbent pads and the like immpregnated with coagulant solution are particularly conformable for use in causing superficial clotting where needed, for example, at the site of a wound or cut. The composition of this invention is made up of a minor but effective proportion of thrombin dissolved in a saline solution to which preservative is or has been added.

The principal preservative is a straight chain 3-6 carbon fully hydroxylated polyol e.g., glycerol, mannitol, sorbitol. Desirably one or more of the non-sulfur containing essential amino acids is present as an additional preservative, and optionally, a polyethylene glycol, preferably of a molecular weight range of 2500 to 6000, is present.

The Sodium chloride content of the coagulant solution is near to isotonic and prevents the rupture of red blood cells when applied to a wound.

A bandage or gauze pad is saturated with the resultant solution and sealed, such as by placing in a sealed container or sealable package, then sealed and is preferably stored at a cool temperature e.g., 2°-8° C. under refrigerated conditions in order to obtain maximum shelf life. The bandage, dressing, pad or the like then can be removed from its container or package and applied directly to the wound or cut without any special preparation or activation of the coagulant composition.

In a preferred embodiment of the present invention, thrombin is dissolved in a saline solution together with lysine, glycerol and polyethylene glycol. Ready-to-use bandages are saturated with the resultant mixture, then individually sealed and stored for future use. In this embodiment, shelf life and effectiveness of the thrombin are prolonged significantly by the combined preservative effect of the glycerol, polyethylene glycol and lysine.

In an alternate preferred embodiment, thrombin is combined with lysine and glycerol and introduced into saline solution, thoroughly mixed or dissolved, then applied immediately to a bandage or pad to completely saturate same. The bandage is sealed by placement in an envelope or other sealable container and stored at a cool temperature so as to minimize evaporation of the solution and to maintain the thrombin in an active state.

Other objects, advantages and features of the present invention will become more readily appreciated and understood when taken together with the following detailed description in conjunction with the accompanying drawings.

BRIEF DESCRIPTION OF THE DRAWINGS

FIG. 1 is a perspective view of a ready-to-use bandage in a sealable envelope and embodying the present invention;

FIG. 2 is a flow diagram of the steps followed in the preparation of the preferred form of prepackaged coagulant in accordance with the present invention; and FIG. 3 is a chart illustrating the comparative stability and clotting time of coagulant solutions prepared in accordance with the present invention.

DETAILED DISCUSSION OF THE INVENTION

In accordance with the present invention, a coagulant solution is prepared by combining 50-2000 units per ml preferably, from 10-100 units of thrombin per ml of coagulant solution together with small amounts of a sulfur-free essential amino acid, the polyhydroxy compound and optionally polyethylene glycol.

The saline coagulant solution may have a final concentration on the order of 0.50% to 0.95% by wt. of sodium chloride.

As has already been indicated the dilute saline coagulant solution is isotonic or near to isotonic in salt concentration to avoid needlessly rupturing red blood cells at the site of the wound.

The amino acid which desirably may be introduced in solid form in proportions of 0.01-0.25 molar. For instance L-lysine may be employed at 0.05 molar, or 0.91325 grams per 100 milliliters of coagulant solution.

One consideration for practice of this invention is that some wounds to which the composition of this invention may be applied are inside body cavities, e.g., the mouth. Dressings and bandages impregnated with the coagulant solution may well be employed to halt bleeding after tooth extraction or other oral surgery. Some of the coagulant solution from the dressing could be ingested. Accordingly, prudence dictates employment of preservative substances that are generally recognized as safe in food stuffs, including notably use only of the essential amino acids (which do not have sulfur moieties) in the coagulant solution. As has already been indicated, the amino acid is present in solution at concentrations of 0.01-0.25 molar.

A limited number of polyhydroxy humectant compounds are contemplated for the coagulant composition of this invention, namely, the linear chain $C_3$-$C_6$ fully hydroxylated polyols, including notably and preferably glycerol, and the six carbon sugar alcohols. Mannitol, sorbitol and mixtures thereof are among the preferred polyols. The polyol content is from 10-50% by wt. of the coagulant solution. Glycerol, the preferred polyol, seems to impart to bandages an anticlot adhesion property, which allows the bandage to be more easily removed from the clot at the wound site. When glycerol is employed, the concentration may be 10-50% by volume, a preferred concentration is about 30% v/v of the coagulant solution.

Presence of the polyethylene glycol is optional, but preferred. When present, the polyethylene glycol is from 0.01-4.0% by weight of the coagulant solution. A polyethylene glycol of molecular weight in the range of 2,500-6,000 is preferred.

Thus, for example, for a preferred embodiment coagulant solution, polyethylene glycol of about 6000 molecular weight is introduced in proportions on the order of 0.2% or 0.2 grams per 100 milliliters of the coagulant solution to saline solution, along with lysine to 0.05 molar, and 6500 International Units of thrombin per 100 ml of coagulant. Glycerol is added in the proportion of about 30 parts by volume of the solution. In the above described resultant solution, the lysine, glycerol and polyethylene glycol each act as protein preservatives, and their combined use has been found to greatly enhance the preservation of the thrombin activity when applied to a pad or other absorbent material.

Thrombin in saline solution is stable for extended periods of time if care is taken to maintain the solution at 2°-8° C. As a practical matter, however, avoiding some likelihood that any batch of thrombin solution will be subjected to ambient or higher temperatures is most difficult. Inevitably some shipments of coagulant products from the site of manufacture would be allowed to sit in an unrefrigerated truck over a holiday or a weekend, or would rest for hours in the sun on a loading dock. If existence of thermally deactivated thrombin has not been recognized prior to use, a failure of the bandage or dressing to induce coagulation will inure to the detriment of the manufacturer. The thrust of this invention is to provide thrombin solutions capable of withstanding deactivation by the thermal conditions to which some shipments might well be subjected. In other words, an important objective herein realized is preparation of coagulant compositions that remain active for extended periods of time, i.e., months, at ambient temperatures.

Test studies indicate that the principal stabilizing or preservative agent is the polyol humectant. The amino acid stabilizes the thrombin to a minor, but cumulative extent. Whether the polyethylene glycol adds to the thermal stability is not certain, but nonetheless presence of the polyethylene glycol is considered desirable and is preferred.

In any event, the compositions of this invention, particularly preferred embodiments thereof have exhibited shelf life in excess of 100 days at 37° C. At 37° C. solutions of thrombin in saline become deactivated within a few days. The compositions of this invention are (thermally) stable enough for distribution of fabricated forms of this invention such as absorbent pads, dressings, bandages and the like from the manufacturing site through normal commercial channels.

To prepare the coagulant composition, the sodium chloride is dissolved in room temperature sterile water (diionized or distilled) at the desired concentration, then some of the saline solution is employed to predissolve the thrombin (which normally is in powder form). Considerably more of the saline solution and all of the polyol used in the batch are mixed, after which the thrombin solution is mixed in. Then all of the (powdered) amino acid e.g., lysine, and, if used, all of the (solid) polyethylene glycol are added on a weight to (final) volume basis and mixed until dissolved. Thereafter adjustment to final volume of coagulant composition is made with more saline solution.

As is illustrated in FIG. 1, the solution is then applied to a bandage 10 so as to thoroughly saturate same. The bandage, for instance, may be comprised of one or more layers of gauze strips as designated at 12 which are encased within a porous plastic film 13 in accordance with conventional practice. The bandage or pad is then sealed in a paper envelope 14 having a foil liner 15 and an inner layer 16 of polyethylene film. The inner film layers 16 have heat sealed borders 17 along their facing edges which are applied together to fully seal the bandage in place. Once packaged as described, the bandage is stored at a cool temperature, preferably on the order of 2° C.-8° C. The steps followed in the preparation of the solution itself and as previously described are illustrated in FIG. 2.

FIG. 3 is a chart illustrating the clotting activity based on stability tests of coagulant solutions in which thrombin is combined with various preservatives in accordance with the present invention. The tests conducted indicate the above described proportions i.e., thrombin present in the amount of 50 to 2,000 units thrombin per milliliter of solution and the polyol on the order of 10 to 50 parts by wt. of coagulant solution. A ratio in excess of 50 parts of glycerol, for example, in the coagulant solution has a tendency to be extremely viscous or thick and seems to delay contact activation; that is, the thrombin becomes less accessible as a clotting agent to the fibronogen. In amounts less than 10 parts of glycerol in the solution, the glycerol loses its preservative effect.

As has already been pointed out, the amino acid range is on the order of 0.01 molar to 0.25 molar. Preferred amino acids are lysine, glycine and isoleucine. The polyethylene glycol range is 0.01-4.0% by weight in the coagulant solution.

In the following Examples of different formulations of the coagulant solution herein provided to illustrate practice of the invention and the results obtainable therefrom, the relative proportions are set forth either as percentage concentrations or weight by volume as indicated.

The test results obtained from coagulants prepared as described by Examples I-VI are illustrated in FIG. 3. It should be appreciated that the proportions and test conditions selected for Examples I-VI were selected so as to provide nearly idealized results demonstrative of the results obtainable by practice of the invention. Preferred embodiment compositions are exemplified in Example VIII.

EXAMPLE I

A coagulant solution was prepared containing the following ingredients:

| Ingredient | Per 100 Milliliters |
| --- | --- |
| Thrombin | 1500 Units |
| Lysine | 0.1 molar |
| Polyethylene Glycol | 0 |
| Glycerol | 30 parts by volume |
| Saline Solution | 0.95% NaCl concentration (Balance) |

The ingredients were thoroughly mixed as described and placed in a vial, then stored at a temperature of 40° C. for the purpose of determining its stability by conducting an accelerated stability test. From the Chart in FIG. 3, based on the accelerated stability tests, after sixty days storage at 40° C., it may be seen that the thrombin in solution remained stable with a capability of clotting blood in less than 10 seconds. The accelerated test is equivalent to eight months shelf life at room temperature or twelve months at 4° C. The results of the accelerated stability tests for the coagulant solutions of Examples I-V are illustrated on FIG. 3.

EXAMPLE II

A coagulant solution was prepared in the following manner:

| Ingredient | Per 100 Milliliters |
| --- | --- |
| Thrombin | 1500 Units |
| Lysine | 0.05 molar |
| Glycerol | 30 parts (by volume) |
| Polyethylene Glycol | 0 |
| Saline Solution | 0.95% NaCl concentration (Balance) |

The ingredients were thoroughly mixed as described and an absorbent pad was saturated with the solution, then packaged and sealed in the manner described so as to be ready for use. In the absence of polyethylene glycol, reduced amounts of lysine appeared to reduce the stability and clotting activity of the solution.

EXAMPLE III

A coagulant solution was prepared as follows:

| Ingredient | Per 100 Milliliters |
| --- | --- |
| Thrombin | 1500 Units |
| Lysine | 0 |
| Polyethylene Glycol | (6000 mw.) 0.2 grams |
| Glycerol | 30 parts (by volume) |

| Ingredient | Per 100 Milliliters |
| --- | --- |
| Saline Solution | 0.95% NaCl concentration (Balance) |

The ingredients were thoroughly mixed as described and an absorbent pad was saturated with the solution, then packaged and sealed so as to be ready for use. In the absence of lysine, clotting time was substantially increased thereby indicating a marked decrease in stability.

EXAMPLE IV

A coagulant solution was prepared in the following manner:

| Ingredient | Per 100 Milliliters |
| --- | --- |
| Thrombin | 1500 Units |
| Lysine | 0.1 Molar |
| Glycerol | 30 parts (by volume) |
| Polyethylene Glycol | 0.2 grams |
| Saline Solution | 0.95% NaCl concentration (Balance) |

The ingredients were thoroughly mixed as described and an absorbent pad was saturated with the solution, then packaged and sealed in the manner described so as to be ready for use. Stability was enhanced and shelf life prolonged markedly by the presence of lysine and polyethylene glycol.

EXAMPLE V

A coagulant solution was prepared in the following manner:

| Ingredient | Per 100 Milliliters |
| --- | --- |
| Thrombin | 1500 Units |
| Lysine | 0.05 molar |
| Glycerol | 30 parts (by volume) |
| Polyethylene Glycol | 0.2 grams per milliliter |
| Saline Solution | 0.9% NaCl concentration (Balance) |

The ingredients were thoroughly mixed as described and an absorbent pad was saturated with the solution, then packaged and sealed in the manner described so as to be ready for use. Notwithstanding, a reduction in lysine, stability of the solution was excellent based on accelerated stability testing.

EXAMPLE VI

A coagulant solution was prepared from the following ingredients as described:

| Ingredient | Per 100 Milliliters |
| --- | --- |
| Thrombin | 1500 units |
| Lysine | 0.05 molar |
| Glycerol | None |
| Polyethylene Glycol | 0.2 grams per milliliter |
| Saline Solution | 0.90% NaCl concentration (Balance) |

The accelerated aging test results were essentially the same as from the coagulant solution of Example III, illustrated as Curve III on FIG. 3.

EXAMPLE VII

A ready-to-use bandage of the type hereinbefore described and shown in FIG. 1 was immersed in a coagulant solution of the composition set forth in Example V until completely saturated. For the purpose of illustration, it is pointed out that for a bandage made from a Telfa pad on the order of 5.08 cm.×7.62 cm.×0.1 cm. the ingredients were present in the pad in the following amounts per cubic centimeter of pad material:

| Thrombin | ≧ than 25.83 units per $CM^3$ |
| --- | --- |
| Polyethylene Glycol | ≧ than 516 microgram per $CM^3$ |
| Glycerine | ≧ than 77 microliter per $CM^3$ |
| Lysine (monohydrochloride) | ≧ than 2.36 milligram per $CM^3$ |

The foregoing concentrations per $CM^3$ are based on even distribution in the Telfa pad.

EXAMPLE VIII

A preferred formulation for practice of this invention is set forth below, which formulation is prepared as described in Example I and employed to impregnate bandages and the like as described in Example VII.

| Ingredient | Proportion |
| --- | --- |
| Water | 70 parts by volume |
| Glycerine | 30 parts by volume |
| L-lysine (monohydrochloride) | 0.913 grams per 100 ml of solution (0.50 M) |
| Sodium Chloride | 0.9 grams/100 ml of solution |
| Polyethylene glycol 6000 Mw | 0.2% gram per 100 ml of solution |
| *Bovine Thrombin (Parke-Davis) | 6500 Int. Units per 100 ml of solution |

*A preferred thrombin range for impregnation of pads such as Telfa pads is 100–125 Int. Units per pad.

EXAMPLE IX

A series of studies were run at 2°–8° C. and at 37° C. with the formulation proportions of Example VIII except as otherwise indicated, variously substituting mannitol and sorbitol for the glycerine and isoleucine and glycine for the L-lysine and omitting the polyethylene glycol and omitting the amino acid.

The control series, i.e., thrombin in saline, deactivated within about one day at 37° C., but exhibited no significant activity loss after 75 days at 2°–8° C., as measured by a test of thrombin clotting time. All the tests with the solutions briefly described hereinafter at 2°–8° C. confirmed the stability of thrombin in solution at low temperatures.

Saline solutions, thrombin with 0.05 M glycine, or isoleucine, or L-lysine but no polyethylene glycol (PEG) or humectant, evidenced at 37° C. some increase in stability, all being stable for at least ten days, without activity loss, but thereafter lost activity rapidly and all solutions becoming completely deactivated within 40 days. In this control test, the isoleucine and glycine performed somewhat better than the L-lysine.

Saline solutions of thrombin (no PEG, no amino acid) with 15% mannitol, or 30% glycerol, or 30% sorbitol exhibited continued thrombin activity at 37° C. for 40 days (sorbitol), and in some tests for 75 days (glycerine and mannitol). Comparable solutions that included 0.2% PEG, and 0.05 M lysine also exhibited stability for at least 40 days, both at room temperature and at 37° C.

A set of saline solutions containing thrombin, 0.2% PEG, 30% glycerin and either 0.05 M of L-lysine, or isoleucine, or glycine exhibited clotting activity after room temperature and 37° C. storage for at least 120 days.

The thrombin employed in the foregoing Examples is a protein substance of bovine origin, and for example, may be of the type formulated and sold by Parke-Davis & Co. of Detroit, Michigan. The commercial preparation, for 10,000 units of thrombin is comprised of about 180–200 milligrams of thrombin powder, 17.4 milligrams of sodium chloride, 15.6 milligrams calcium chloride, 19 milligrams glycine and 0.2 milligrams of benzethonium chloride.

After fabrication, including sealing, as has been described, the resultant saturated pads can be shipped at normal temperatures, although it is advisable to store under refrigerated conditions so as to prolong the life of the solution, particularly to maintain the thrombin activity as long as possible. In any case, the effectiveness of the coagulant solution can be determined when the package is opened. If the solution has dried, the thrombin will not effectively act as a clotting agent.

The chart, FIG. 3, demonstrates the marked increase in shelf life of thrombin when combined in accordance with Examples I, IV and V. Accelerated studies at 40° C. indicate that the above formulations provide stability of thrombin to be equivalent to at least an eight month shelf life at room temperature (+22° C.) or at least a twelve month shelf life at refrigerated temperature (2° C.–8° C.). The accelerated studies at 40° C. also indicate that the stability of the thrombin molecule is cumulatively enhanced by all three ingredients, glycerol or glycerine, polyethylene glycol (PEG) and the sulfur free essential amino acid. If the optional PEG is omitted, the amino acid content in the formulation should be at least double what is in the preferred formulation (from 0.05 molar to 0.1 molar) to maintain adequate stability of thrombin in the absence of polyethylene glycol.

From the foregoing, it has been found that the prepackaged protein coagulant solution as described not only is a highly effective manner and means of clotting when applied to a wound, but avoids time-consuming and expensive mixing and preparation of a coagulant each time that it is required for individual use. On the other hand, the shelf life of the coagulant solutions described herein are sufficient to assure effectiveness after extended storage time periods. When applied to a wound, the thrombin even when present in minor proportions in a dilute solution is capable of acting very low down in the clotting sequence as long as the patient has normal circulating fibrinogen.

Although ready-to-use bandages and a specific method of forming same have been described, it will be appreciated that various modifications and changes may be made therein without departing from the spirit and scope of the invention as defined by the following claims.

I claim:

1. A coagulant adaptable for use as a dressing for wounds comprising a solution of 50–2000 units of thrombin per ml of an aqueous solution containing sodium chloride in about isotonic quantities and from 10–50% by weight of a straight chain 3 to 6 carbon fully hydroxylated polyol.

2. The coagulant of claim 1 wherein the solution contains also a sulfur-free essential amino acid in molar proportions of 0.01–0.25.

3. The coagulant composition of claim 2 wherein said amino acid is lysine.

4. The coagulant composition of claim 2 wherein said solution contains a combination of glycerol and lysine.

5. The coagulant of claim 2 wherein the solution contains also from 0.1–4.0% by wt. of a polyethylene glycol of a molecular weight in the range of 2,500–6000.

6. The coagulant composition of claim 5 where said solution contains glycerol, lysine and polyethylene glycol.

7. The coagulant composition of claim 1 wherein glycerol is present as about 30 parts by volume of the solution.

8. A prepackaged coagulant material adaptable for use as bandages, dressings and the like for wounds comprising in combination:
a solution of thrombin containing sodium chloride in about isotonic proportions together with from 10–50% by weight of a straight chain 3 to 6 carbon fully hydroxylated polyol, and
an absorbent material saturated by said solution, and sealing means hermetically sealing said saturated absorbent material.

9. The prepackaged coagulant material of claim 8, said thrombin being present in the range of 25 to 250 units per cc. of absorbent material.

10. The prepackaged coagulant material of claim 8, said solution including therein a sulfur-free essential amino acid in molar proportions of 0.01–0.25.

11. The prepackaged coagulant material of claim 10, said solution containing lysine.

12. The prepackaged coagulant material of claim 11, said solution containing glycerol and lysine.

13. The prepackaged coagulant material of claim 10, said solution containing from 0.1–4.0% by weight of a polyethylene glycol of molecular weight in the range of 2,500–6,000.

14. The prepackaged coagulant material of claim 13, said solution containing glycerol, lysine and polyethylene glycol.

15. The prepackaged coagulant material of claim 8, said solution including therein glycerol as about 30 parts volume of the solution.

16. The prepackaged coagulant material of claim 8 in a ready-to-use bandage form containing about 25.0 units of thrombin per $CM^3$ of pad material.

* * * * *